United States Patent
Pi et al.

(10) Patent No.: US 10,912,720 B2
(45) Date of Patent: Feb. 9, 2021

(54) CO-EMULSIFICATION COMPOSITION CONTAINING VARIOUS EMULSIFICATION PARTICLE SIZES AND METHOD FOR PREPARING SAME

(71) Applicant: AMOREPACIFIC CORPORATION, Seoul (KR)

(72) Inventors: Bong Soo Pi, Yongin-si (KR); Jin Nam, Yongin-si (KR); Sung Ii Park, Yongin-si (KR); Soon Ae An, Yongin-si (KR); Byung Young Kang, Yongin-si (KR); Sang Hoon Han, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 15/540,720

(22) PCT Filed: Dec. 29, 2015

(86) PCT No.: PCT/KR2015/014387
§ 371 (c)(1),
(2) Date: Jun. 29, 2017

(87) PCT Pub. No.: WO2016/108567
PCT Pub. Date: Jul. 7, 2016

(65) Prior Publication Data
US 2017/0367936 A1 Dec. 28, 2017

(30) Foreign Application Priority Data

Dec. 31, 2014 (KR) .................. 10-2014-0194546
Dec. 28, 2015 (KR) .................. 10-2015-0187717

(51) Int. Cl.
| A61K 8/06 | (2006.01) |
| A61K 8/02 | (2006.01) |
| A61K 8/81 | (2006.01) |
| A61Q 19/00 | (2006.01) |

(52) U.S. Cl.
CPC .............. *A61K 8/06* (2013.01); *A61K 8/0287* (2013.01); *A61K 8/062* (2013.01); *A61K 8/068* (2013.01); *A61K 8/8111* (2013.01); *A61K 8/8117* (2013.01); *A61Q 19/00* (2013.01); *A61K 2800/21* (2013.01); *A61K 2800/412* (2013.01); *A61K 2800/57* (2013.01); *A61K 2800/594* (2013.01); *A61K 2800/624* (2013.01); *A61K 2800/654* (2013.01)

(58) Field of Classification Search
None
See application file for complete search history.

(56) References Cited

U.S. PATENT DOCUMENTS

| 5,753,242 A * | 5/1998 | Nakamura ........... A61K 8/0212 424/401 |
| 6,709,662 B1 * | 3/2004 | Gers-Barlag ............ A61K 8/06 424/400 |
| 2006/0204469 A1 * | 9/2006 | Spengler ................. A61K 8/06 424/70.31 |
| 2011/0195030 A1 * | 8/2011 | Mumper .............. A61K 9/1075 424/9.32 |
| 2014/0336275 A1 | 11/2014 | Ehrman et al. |
| 2015/0291742 A1 * | 10/2015 | Lee .......................... C08F 8/12 524/577 |

FOREIGN PATENT DOCUMENTS

| EP | 3150191 A1 | 4/2017 | |
| KR | 1020090073368 A | 7/2009 | |
| KR | 101299148 B1 | 8/2013 | |
| KR | 1020130116879 | 10/2013 | |
| KR | 1020140073211 A | 6/2014 | |
| KR | 1020140091556 A | 7/2014 | |
| WO | 2008058297 | 5/2008 | |
| WO | WO-2008058297 A2 * | 5/2008 | .............. C08J 3/246 |
| WO | 2012044929 | 4/2012 | |
| WO | 2013074931 A1 | 5/2013 | |
| WO | 2015183042 A1 | 12/2015 | |

OTHER PUBLICATIONS

Extended European Search Report—European Application No. EP15875661.9 dated May 24, 2018.
International Search Report with English Translation for International Application No. PCT/KR2015/014387 dated Apr. 8, 2016.
Korean Notice of Allowance—Korean Application No. 10-2015-0187717 dated Aug. 2, 2018.
Nakahara Akio, et al., "Ostwald ripening in open System", Physical research, Dec. 20, 1991, vol. 57, No. 3, pp. 419-420.
Taiwanese Office Action—Taiwanese Application No. 104144431 dated Aug. 14, 2019.

* cited by examiner

*Primary Examiner* — Susan T Tran
*Assistant Examiner* — William Graigo
(74) *Attorney, Agent, or Firm* — Cantor Colburn LLP

(57) ABSTRACT

Disclosed are: a co-emulsified composition containing different emulsification particle sizes; and a method for preparing the same. The co-emulsified composition contains an amphipathic anisotropic power and a surfactant, thereby allowing emulsification particles with different sizes to coexist in one dosage form, and thus a co-emulsified composition can be provided that simultaneously implements two or more feelings of use or physical characteristics.

8 Claims, 3 Drawing Sheets

【Fig. 1】
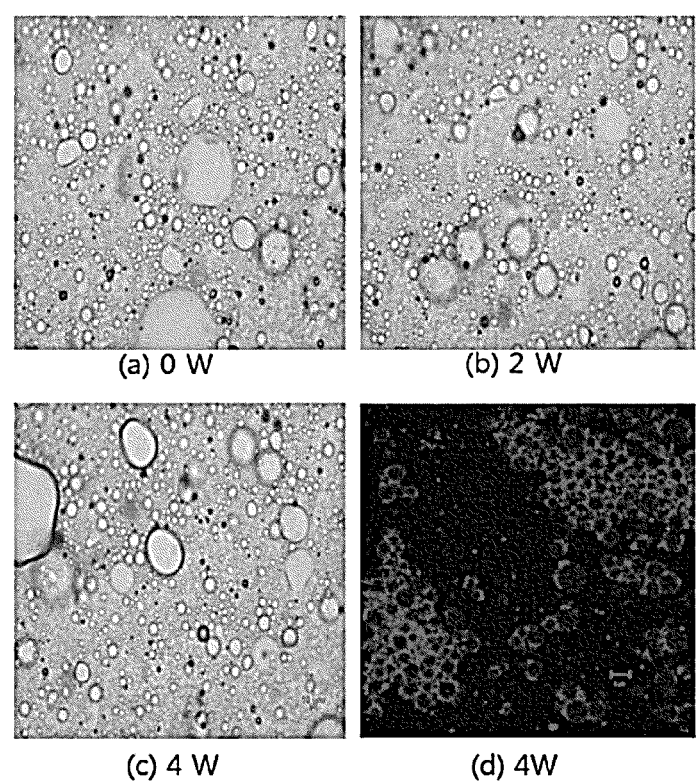

[Fig. 2]
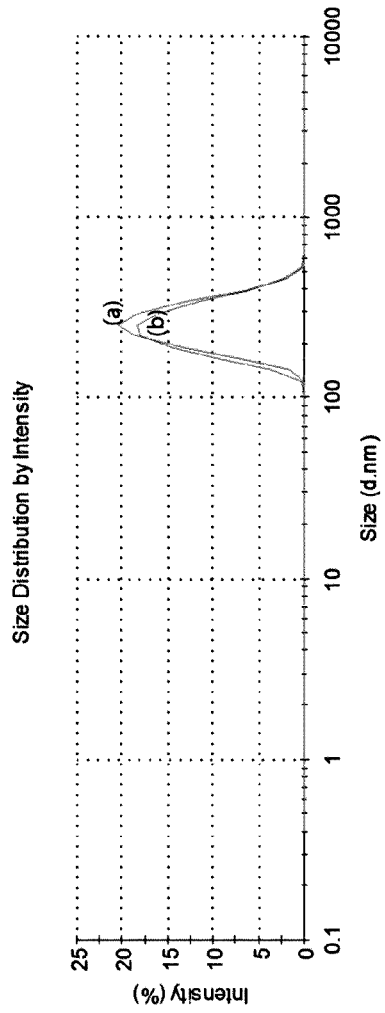

[Fig. 3]
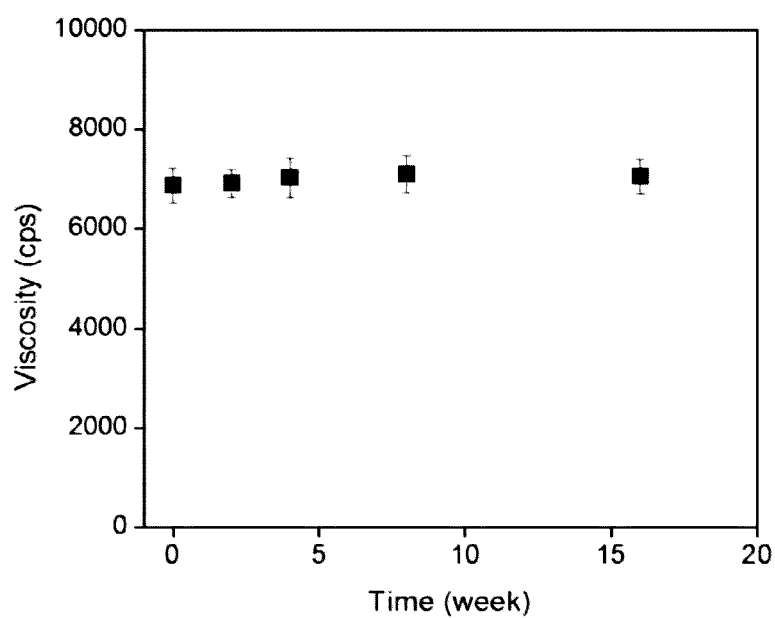

CO-EMULSIFICATION COMPOSITION CONTAINING VARIOUS EMULSIFICATION PARTICLE SIZES AND METHOD FOR PREPARING SAME

TECHNICAL FIELD

The present disclosure relates to a hybrid emulsion composition that includes different emulsion particle sizes coexisting in an emulsion system and shows properties of each emulsion particle, and a method for preparing the same.

BACKGROUND ART

According to the related art, preparation of an emulsion composition for cosmetics have been focused on making the emulsion particle size small and uniform within a range of several micrometers or less to obtain an emulsion composition stably without coalescence of particles. This is because it is important to prevent the so-called Ostwald ripening phenomenon (coalescence of particles caused by a difference in emulsion particle sizes) so as to ensure a stable emulsion system.

An emulsion system shows its fundamental properties according to its emulsion particle size and a different particle size provides a different feeling of use. For example, nano-size (several hundreds of nanometers) emulsion particles show a moisturizing and nourishing effect. Emulsion particles having a micro-size (several micrometers) that is a typical emulsion particle size in most cosmetic composition show soft spreadability.

However, when different emulsion particles are to be present together in a single formulation, a problem related with emulsion formulation stability (such as coalescence) occurs and thus such different emulsion particles have been mixed merely at an extremely limited ratio. In addition, in the case of the conventional multiple emulsion systems, such as water-in-oil-in-water or oil-in-water-in-oil emulsion systems, smaller emulsion particles are present in emulsion particles in nature, and thus preparation and reproducibility are limited to and industrial applicability is also limited.

DISCLOSURE

Technical Problem

A technical problem to be solved by the present disclosure is to provide a hybrid emulsion composition that solves the problems of coalescence caused by non-uniformity of different emulsion particle sizes and unstability of emulsion particles and allows coexistence of emulsion particles having different sizes to realize at least two different feelings of use or physical properties at the same time.

Technical Solution

In one general aspect, there is provided an emulsion composition having different emulsion particle sizes, the emulsion composition including macroemulsion particles having a size of 1 μm-100 μm and nanoemulsion particles having a size of 100 nm-900 nm, wherein the macroemulsion particles include amphiphilic anisotropic powder; the amphiphilic anisotropic powder includes a first hydrophilic polymer spheroid and a second hydrophobic polymer spheroid; the first and second polymer spheroids are bound to each other with a structure in which one polymer spheroid at least partially infiltrates the other polymer spheroid; the first polymer spheroid has a core-shell structure; and the shell has a functional group.

According to an embodiment, the macroemulsion particles and the nanoemulsion particles are present at a ratio of 5-9:5-1.

According to another embodiment, the second polymer spheroid and the core of the first polymer spheroid include a vinyl polymer, and the shell of the first polymer spheroid may include a copolymer of a vinyl monomer with a functional group.

According to still another embodiment, the vinyl polymer may include polystyrene.

According to still another embodiment, the functional group may be siloxane.

According to still another embodiment, the shell of the first polymer spheroid may further include a hydrophilic functional group introduced thereto.

According to still another embodiment, the functional group may be at least one selected from the group consisting of carboxylic acid group, sulfone group, phosphate group, amino group, alkoxy group, ester group, acetate group, polyethylene glycol group and hydroxyl group.

According to still another embodiment, the amphiphilic anisotropic powder may have a symmetric shape, asymmetric snowman shape or asymmetric reverse snowman shape on the basis of the binding portion where the first polymer spheroid and the second polymer spheroid are bound to each other.

According to yet another embodiment, the amphiphilic anisotropic powder may have a particle size of 100-1500 nm.

In another general aspect, there is provided a method for preparing a hybrid emulsion composition, including: forming each of an emulsion composition containing an amphiphilic anisotropic powder for preparing macroemulsion particles having a size of 1 μm-100 μm and an emulsion composition containing a surfactant for preparing nanoemulsion particles having a size of 100 nm-900 nm, and mixing the emulsion compositions with each other.

In still another general aspect, there is provided a method for preparing a hybrid emulsion composition, including: (a) introducing amphiphilic anisotropic powder for preparing macroemulsion particles having a size of 1 μm-100 μm to an aqueous phase part and dispersing the powder therein; (b) introducing oil to carry out preliminary emulsification; (c) introducing a thickener and neutralizer and dispersing them; and (d) introducing a surfactant for preparing nanoemulsion particles having a size of 100 nm-900 nm and oil to carry out secondary emulsification.

Advantageous Effects

According to the embodiments of the present disclosure, a Pickering surfactant system using amphiphilic anisotropic powder and a conventional emulsion system using a surfactant are combined with each other to provide a heterogeneous emulsion system having no impact on each other. In this manner, it is possible to provide a hybrid emulsion composition including different sizes of emulsion particles that coexist in a single formulation and showing at least two different feelings of use and physical properties at the same time.

In addition, the emulsion composition disclosed herein is not a multiple emulsion system in which another type of emulsion particles are present in one type of emulsion particles, but a single formulation in which different sizes of emulsion particles are present independently from each other so that at least two different feelings of use derived from each of the emulsion particles may be realized. Each of the emulsion particles coexist in the emulsion composition without coalescence, and thus the emulsion composition ensures significantly higher stability as compared to the conventional multiple emulsion systems and may be applicable to various formulations and products.

DESCRIPTION OF DRAWINGS

FIG. 1 shows microscopic images of the hybrid emulsion composition obtained by the individual emulsion mixing method according to an embodiment, wherein (a) shows a formulation obtained from emulsion particles using anisotropic powder (size: about several tens of micrometers) and nanoemulsion particles (size: about 200 nm) using a general surfactant, right after the preparation thereof, (b) and (c) show the emulsion particle sizes after storing the formulation for 2 weeks and 4 weeks, respectively, at a high temperature of 45° C., and (d) shows the result obtained by fluorescence imaging of the nanoemulsion in the sample of (c).

FIG. 2 shows particle size distribution of the hybrid emulsion composition obtained by the individual emulsion mixing method according to an embodiment, wherein (a) shows the particle size distribution right after the preparation (average: approximately 200 nm), (b) shows the particle size distribution measured after 4 weeks (average: approximately 190 nm), and thus no significant difference is observed.

FIG. 3 shows a change in viscosity of the hybrid emulsion composition obtained by the individual emulsion mixing method according to an embodiment as a function of time, which suggests that the formulation stability is maintained with time over a range of temperatures (−15 to 60° C.) without a significant change in viscosity.

BEST MODE

Exemplary embodiments now will be described more fully hereinafter with reference to the accompanying drawings, in which exemplary embodiments are shown. This disclosure may, however, be embodied in many different forms and should not be construed as limited to the exemplary embodiments set forth therein. Rather, these embodiments are provided so that this disclosure will be thorough and complete, and will fully convey the scope of the present disclosure to those skilled in the art. In the drawings, the shape, size and regions, and the like, of the drawing may be exaggerated for clarity. In addition, although a part of constitutional elements is shown for convenience of description, the remaining part may be understood with ease by those skilled in the art. Further, it will be understood by those skilled in the art that various changes in form and details may be made thereto without departing from the scope of this disclosure as defined by the appended claims.

As used herein, "substituted" means that at least one hydrogen atom of the functional group described herein is substituted with a halogen atom (F, Cl, Br or I), hydroxyl group, nitro group, imino group (=NH, =NR, wherein R is a C1-C10 alkyl group), amidino group, hydrazine or hydrazine group, carboxyl group, substituted or non-substituted C1-C20 alkyl group, substituted or non-substituted C3-C30 heteroaryl group, or substituted or non-substituted C2-C30 heterocycloalkyl group, unless otherwise stated.

As used herein, "(meth)acryl" means acryl and/or methacryl.

As used herein, the particle size of amphiphilic anisotropic powder is measured as the maximum length that is the largest length of the powder particles. As used herein, the particle size range of amphiphilic anisotropic powder means that at least 95% of the amphiphilic anisotropic powder present in a composition belongs to the corresponding range.

As used herein, the average particle diameter of emulsion particles means the average of diameter of each particle. As used herein, the average particle diameter range of emulsion particles means that at least 95% of the emulsion particles present in a composition belongs to the corresponding range.

In one aspect, there is provided an emulsion composition having different emulsion particle sizes, the emulsion composition including emulsion particles having a size of 100 nm-100 μm, wherein the amphiphilic anisotropic powder includes a first hydrophilic polymer spheroid and a second hydrophobic polymer spheroid; the first and second polymer spheroids are bound to each other with a structure in which one polymer spheroid at least partially infiltrates the other polymer spheroid; the first polymer spheroid has a core-shell structure; and the shell has a functional group.

According to an embodiment, the emulsion composition may include emulsion particles having an average particle diameter of 100 nm-90 μm. For example, the emulsion particles may have an average particle diameter of 100 nm-1000 nm or 100 nm-900 nm.

In another aspect, there is provided an emulsion composition having different emulsion particle sizes, the emulsion composition including macroemulsion particles having a size of 1 μm-100 μm and nanoemulsion particles having a size of 100 nm-900 nm, wherein the macroemulsion particles include amphiphilic anisotropic powder; the amphiphilic anisotropic powder includes a first hydrophilic polymer spheroid and a second hydrophobic polymer spheroid; the first and second polymer spheroids are bound to each other with a structure in which one polymer spheroid at least partially infiltrates the other polymer spheroid; the first polymer spheroid has a core-shell structure; and the shell has a functional group.

The hybrid emulsion composition refers to an emulsion composition including emulsion particles having different sizes.

The hybrid emulsion composition including emulsion particles having different sizes realizes properties of each emulsion particle. Particularly, a cosmetic composition including base emulsion particles (several micrometers) in combination with nanoemulsion particles (several hundreds of nanometers) shows soft spreadability derived from the emulsion particles having a size of several micrometers and a moisturizing and nourishing feeling derived from the nanoemulsion particles having a size of several hundreds of nanometers. Since the emulsion composition includes amphiphilic anisotropic powder, it maximizes the difference in sizes of emulsion particles so that the macroemulsion particles having a size of 1 μm-100 μm may be mixed stably with the nanoemulsion particles having a size of 100 nm-1 μm and the properties of each type of particles may be felt actually by the users. In other words, the emulsion composition may be provided as a 2-in-1 or 3-in-1 type formulation having unique double feelings of use, and thus may show a moisturizing feeling derived from the watering of macroemulsion particles and then a nourishing feeling derived from the applicability of the smaller emulsion particles.

Since the hydrophobic part and hydrophilic part of the amphiphilic anisotropic powder have different orientability against the interface, it is possible to form macroemulsion particles and to provide a formulation having an excellent feeling of use. It is difficult to form stabilized macroemulsion particles having a particle diameter of several tens of micrometers by using a molecular-level surfactant according to the related art, and the surfactant provides an interface film having a thickness of about several nanometers. However, in the case of the amphiphilic anisotropic powder disclosed herein, the thickness of the interface film increases to about several hundreds of nanometers and a stabilized interface film is formed by virtue of the strong binding among the powder particles, thereby improving emulsion stability significantly.

As used herein, a spheroid means a single body formed of polymers. For example, it may have a spherical or ellipsoidal shape and a micro-scale or nano-scale long axis length based on the largest length in the section of the body.

According to an embodiment, the amphiphilic anisotropic powder may be present in an amount of 0.1-15 wt % based on the total weight of the hybrid emulsion composition. According to another embodiment, the chemically anisotropic powder may be present in an amount of 1-5 wt % based on the total weight of the emulsion composition. Particularly, the chemically anisotropic powder may be present in an amount of at least 1 wt %, at least 2 wt %, at least 4 wt %, at least 6 wt %, at least 8 wt %, at least 10 wt % or at least 12 wt %, and at most 15 wt %, at most 12 wt %, at most 10 wt %, at most 8 wt %, at most 6 wt %, at most 4 wt % or at most 2 wt %. It is possible to control the size of emulsion particles from several micrometers to several tens or several hundreds of micrometers by adjusting the content of chemically anisotropic powder.

According to an embodiment, the macroemulsion particles and the nanoemulsion particles are present at a ratio of 5-9:5-1, or 7-9:3-1.

According to another embodiment, the second polymer spheroid and the core of the first polymer spheroid include vinyl polymers, and the shell of the first polymer spheroid may include a copolymer of a vinyl polymer with a functional group.

According to still another embodiment, the vinyl polymer may include a vinyl aromatic polymer, particularly polystyrene.

According to still another embodiment, the functional group may be siloxane.

According to still another embodiment, the shell of the first polymer spheroid may have a hydrophilic functional group introduced thereto.

According to still another embodiment, the hydrophilic functional group may be a negatively charged or positively charged functional group or polyethylene glycol (PEG)-based functional group, and may include at least one selected from the group consisting of carboxylic acid group, sulfone group, phosphate group, amino group, alkoxy group, ester group, acetate group, polyethylene glycol group and hydroxyl group.

According to still another embodiment, the amphiphilic anisotropic powder may have a symmetric shape, asymmetric snowman shape or asymmetric reverse snowman shape on the basis of the binding portion where the first polymer spheroid and the second polymer spheroid are bound to each other.

According to yet another embodiment, the amphiphilic anisotropic powder may have a particle size of 100-1500 nm. In a variant, the amphiphilic anisotropic powder may have a particle size of 100-500 nm, or 200-300 nm. Herein, the particle size means the largest length of the amphiphilic powder. Particularly, the amphiphilic powder may have a particle size of at least 100 nm, at least 200 nm, at least 300 nm, at least 400 nm, at least 500 nm, at least 600 nm, at least 700 nm, at least 800 nm, at least 900 nm, at least 1000 nm, at least 1100 nm, at least 1200 nm, at least 1300 nm or at least 1400 nm, and at most 1500 nm, at most 1400 nm, at most 1300 nm, at most 1200 nm, at most 1100 nm, at most 1000 nm, at most 900 nm, at most 800 nm, at most 700 nm, at most 600 nm, at most 500 nm, at most 400 nm, at most 300 nm or at most 200 nm.

In another general aspect, there is provided a method for preparing the hybrid emulsion composition, including: forming each of an emulsion composition containing an amphiphilic anisotropic powder for preparing macroemulsion particles having a size of 1 μm-100 μm and an emulsion composition containing a surfactant for preparing nanoemulsion particles having a size of 100 nm-900 nm, and mixing the emulsion compositions with each other. Thus, the method is an individual emulsion mixing method that includes simply mixing emulsion compositions each of which is prepared separately. Therefore, it is possible to freely control the mixing ratio of the emulsion compositions.

According to an embodiment, the thickener may be at least one selected from the group consisting of carbomer, carbopol, gelatin, xanthan gum, natural cellulose, hydroxyethyl cellulose and methyl cellulose.

According to another embodiment, the neutralizer may be at least one selected from the group consisting of triethyl amine (TEA), sodium hydroxide (NaOH), potassium hydroxide (KOH) and cationic metals.

According to still another embodiment, the surfactant may be at least one selected from the group consisting of lecithin, Polysorbate 80, sorbitan stearate, sorbitan sesquioleate, polyoxyethylene phytosterol, glyceryl monostearate, hydrogenated soybean phospholipid, PEG-10 dimethicone, cetyl PEG/PPG-10/1 dimethicone, polyoxyethylene methylpolysiloxane copolymer, poly(oxyethyleneoxypropylene) methyl polysiloxane copolymer and polyoxypropylene methylpolysiloxane copolymer.

According to still another embodiment, the hybrid emulsion composition may be a cosmetic composition. Particularly, the cosmetic composition may be at least one of oil-in-water (O/W) type, water-in-oil (W/O) type, W/O/W type or O/W/O formulations.

The cosmetic composition may be an oil-in-water (O/W) type formulation including the amphiphilic anisotropic powder, an oil phase part and an aqueous phase part at a weight ratio of 0.1-15:5-60:10-80. In a variant, the cosmetic composition may be an oil-in-water (O/W) type formulation including the amphiphilic anisotropic powder, an oil phase part and an aqueous phase part at a weight ratio of 0.1-5:15-40:50-80. In another variant, the cosmetic composition may be a water-in-oil (W/O) type formulation including the amphiphilic anisotropic powder, an oil phase part and an aqueous phase part at a weight ratio of 1-15:50-80:10-30. The oil phase part may include at least one selected from the group consisting of liquid oil and fat, solid oil and fat, wax, hydrocarbon oil, higher fatty acids, higher alcohols, synthetic ester oil and silicon oil.

According to yet another embodiment, the amphiphilic anisotropic powder may be added in combination with the aqueous phase part to provide a cosmetic composition.

In still another aspect, there is provided a method for preparing amphiphilic anisotropic powder, including: (1) agitating a first monomer and a polymerization initiator to form a core of a first polymer spheroid; (2) agitating the formed core of a first polymer spheroid with a first monomer, a polymerization initiator and a functional group-containing monomer to form a first polymer spheroid having a core-shell structure; (3) agitating the formed first polymer spheroid having a core-shell structure with a second monomer and a polymerization initiator to obtain anisotropic powder in which a second polymer spheroid is formed; and (4) introducing a hydrophilic functional group to the obtained anisotropic powder.

In steps (1), (2) and (3), the agitation may be rotary agitation. Since homogeneous mechanical mixing is required together with chemical modification in order to produce uniform particles, rotary agitation is preferred. The rotary agitation may be carried out in a cylindrical reactor but is not limited thereto.

Herein, the internal design of the reactor significantly affects powder formation. The size and position of the baffles of the cylindrical reactor and the distance from an impeller have a significant effect upon the uniformity of the particles to be produced. Preferably, the interval between the internal blade and the blade of an impeller is minimized to make convection flow and intensity thereof uniform, the powdery reaction mixture is introduced to a level lower than the blade length, and the impeller is maintained at a high rotation speed. The rotation speed may be 200 rpm or higher, and the ratio of the diameter to the height of the reactor may be 1-3:1-5. Particularly, the reactor may have a diameter of 10-30 cm and a height of 10-50 cm. The reactor may have a size variable in proportion to the reaction capacity. In addition, the cylindrical reactor may be made of ceramics, glass or the like. The agitation is carried out preferably at a temperature of 50-90° C.

Simple mixing in a cylindrical rotary reactor allows production of uniform particles, requires low energy consumption and provides maximized reaction efficiency, and thus is amenable to mass production. The conventional tumbling method including rotation of a reactor itself causes inclination of the whole part of the reactor with a certain angle and rotation at a high speed, and thus requires high energy consumption and limits the reactor size. Due to such limitation in reactor size, the output is limited to a small amount of approximately several tens of milligrams to several grams. Thus, the conventional tumbling method is not suitable for mass production.

According to an embodiment, the first monomer and the second monomer may be the same or different, and particularly may be a vinyl monomer. In addition, the first monomer added in step (2) may be the same as the first monomer used in step (1) and the initiator used in each step may be the same or different.

According to another embodiment, the vinyl monomer may be a vinyl aromatic monomer. The vinyl aromatic monomer may be substituted or non-substituted styrene, such as at least one selected from the group consisting of styrene, alpha-methylstyrene, alpha-ethylstyrene and para-methylstyrene.

According to still another embodiment, the polymerization initiator may be a radical polymerization initiator. Particularly, the polymerization initiator may be at least one selected from peroxide-based and azo-based initiators. In addition, ammonium persulfate, sodium persulfate or potassium persulfate may be used. The peroxide-based radical polymerization initiator may be at least one selected from the group consisting of benzoyl peroxide, lauryl peroxide, cumene hydroperoxide, methylethyl ketone peroxide, t-butyl hydroperoxide, o-chlorobenzoyl peroxide, o-methoxylbenzoyl peroxide, t-butylperoxy-2-ethylhexanoate and t-butylperoxy isobutyrate. The azo-based radical polymerization initiator may be at least one selected from the group consisting of 2,2-azobisisobutyronitrile, 2,2'-azobis(2-methylisobutyronitrile) and 2,2'-azobis(2,4-dimethylvaleronitrile).

According to still another embodiment, in step (1), the first monomer and the polymerization initiator may be mixed at a weight ratio of 100-250:1.

In a variant, in step (1), a stabilizer is added together with the first monomer and the polymerization initiator in such a manner that the first monomer, polymerization initiator and the stabilizer may be mixed at a weight ratio of 100-250:1: 0.001-5. The size and shape of the powder is determined by controlling the size of the first polymer spheroid in step (1), and the size of the first polymer spheroid may be controlled by the ratio of the first monomer, initiator and the stabilizer. In addition, it is possible to increase the uniformity of anisotropic powder by mixing the first monomer, polymerization initiator and the stabilizer within the above-defined ratio.

According to an embodiment, the stabilizer may be an ionic vinyl monomer, and particularly sodium 4-vinylbenzene sulfonate may be used. The stabilizer prevents swelling of the particles, and imparts positive or negative charges to the powder surface, thereby preventing coalescence (binding) of the particles electrostatically.

When the amphiphilic powder has a size of 200-250 nm, it may be obtained from the first polymer spheroid including the first monomer, initiator and the stabilizer at a ratio of 110-130:1:2-4, particularly 115-125:1:2-4, and more particularly 120:1:3.

In addition, when the amphiphilic powder has a size of 400-450 nm, it may be obtained from the first polymer spheroid including the first monomer, initiator and the stabilizer at a ratio of 225-240:1:1-3, particularly 230-235: 1:1-3, and more particularly 235:1:2.

Further, when the amphiphilic powder has a size of 1100-1500 nm, it may be obtained from the first polymer spheroid prepared by reacting the first monomer, initiator and the stabilizer at a ratio of 110-130:1:0, particularly 115-125:1:0, and more particularly 120:1:0.

In addition, amphiphilic powder having an asymmetric snowman shape may be obtained from the first polymer spheroid prepared by reacting the first monomer, initiator and the stabilizer at a ratio of 100-140:1:8-12, particularly 110-130:1:9-11, and more particularly 120:1:10.

Further, amphiphilic powder having an asymmetric reverse snowman shape may be obtained from the first polymer spheroid prepared by reacting the first monomer, initiator and the stabilizer at a ratio of 100-140:1:1-5, particularly 110-130:1:2-4, and more particularly 120:1:3.

According to still another embodiment, the functional group-containing monomer in step (2) may be a siloxane-containing compound. Particularly, it may be a siloxane-containing (meth)acrylate monomer, and more particularly may be at least one selected from the group consisting of 3-(trimethoxysilyl)propyl acrylate, 3-(trimethoxysilyl)propyl methacrylate, vinyltriethoxysilane and vinyltrimethoxysilane.

According to still another embodiment, in step (2), the first monomer, polymerization initiator and the functional group-containing monomer may be mixed at a weight ratio of 80-98:0.2-0.8:2-20. In a variant, the first monomer, polymerization initiator and the functional group-containing monomer may be mixed at a weight ratio of 160-200:1:6-40. It is possible to control the coating degree according to the reaction ratio, and the coating degree determines the shape of amphiphilic anisotropic powder. When the first monomer, polymerization initiator and the functional group-containing monomer are used within the above-defined ratio, the coating thickness is increased by about 10-30%, particularly approximately 20%, based on the initial thickness. In this case, formation of powder proceeds smoothly without problems, such as a failure in formation of powder caused by excessively thick coating or multi-directional formation of powder caused by excessively thin coating. In addition, it is possible to increase the uniformity of anisotropic powder within the above weight ratio.

According to still another embodiment, in step (3), the second monomer and polymerization initiator may be mixed at a weight ratio of 200-250:1.

In a variant, in step (3), a stabilizer may be added together with the second monomer and polymerization initiator in such a manner that the second monomer, polymerization initiator and the stabilizer may be mixed at a weight ratio of 200-250:1:0.001-5. Particular examples of the stabilizer are the same as described above. It is possible to increase the uniformity of anisotropic powder within the above weight ratio.

According to still another embodiment, in step (3), the second monomer may be mixed in an amount of 40-300 parts by weight based on 100 parts by weight of the first polymer spheroid. Particularly, when the content of the second monomer is 40-100% based on the weight of the first polymer spheroid, asymmetric snowman-like powder is obtained. When the content of the second monomer is 100-150% or 110-150% based on the weight of the first polymer spheroid, symmetric powder is obtained. In addition, when the content of the second monomer is 150-300% or 160-300% based on the weight of the first polymer spheroid, asymmetric reverse snowman-like powder is obtained. It is possible to increase the uniformity of anisotropic powder within the above weight ratio.

According to still another embodiment, in step (4), the hydrophilic functional group may be introduced by using a silane coupling agent and reaction modifier, but is not limited thereto.

According to still another embodiment, the silane coupling agent may be at least one selected from the group consisting of (3-aminopropyl)trimethoxysilane, N-[3-(trimethoxysilyl)propyl]ethylene diamine, N-[3-(trimethoxysilyl)propyl]ethylenediammonium chloride, (N-succinyl-3-aminopropyl)trimethoxysilane, 1-[3-(trimethoxysilyl)propyl]urea and 3-[(trimethoxysilyl)propyloxy]-1,2-propanediol. Particularly, the silane coupling agent may be N-[3-(trimethoxysilyl)propyl]ethylene diamine.

According to yet another embodiment, the reaction modifier may be ammonium hydroxide.

According to the related art, many attempts have been made to increase the surface active property of spherical powder particles used for Pickering by imparting amphiphilic surface active property thereto. This may be exemplified by Janus spherical particles. However, such particles are geometrically limited and have a problem in terms of uniform mass production, and thus cannot be applied practically. On the contrary, the method for preparing amphiphilic anisotropic powder disclosed herein uses no cross-linking agent, thereby causing no agglomeration and providing high yield and uniformity. In addition, the method disclosed herein uses a simple agitation process and is more amenable to mass production as compared to a tumbling process. Particularly, the method disclosed herein is advantageous in that it allows production of nano-size particles having a size of 300 nm or less in a large scale of several tens of grams and several tens of kilograms.

MODE FOR INVENTION

Exemplary embodiments now will be described more fully hereinafter with reference to the accompanying drawings, in which exemplary embodiments are shown. This disclosure may, however, be embodied in many different forms and should not be construed as limited to the exemplary embodiments set forth therein.

Preparation Example 1. Preparation of Polystyrene (PS) First Polymer Spheroid

Styrene as a monomer, sodium 4-vinylbenzene sulfonate as a stabilizer and azobisisobutyronitrile (AIBN) as an initiator are mixed in an aqueous phase and are allowed to react at 75° C. for 8 hours. The reaction is carried out by agitating the reaction mixture in a cylindrical reactor having a diameter of 11 cm and a height of 17 cm and made of glass under a speed of 200 rpm.

Preparation Example 2. Preparation of Coated First Polymer Spheroid Having Core-Shell (CS) Structure The polystyrene (PS) first polymer spherical particles obtained as described above is mixed with styrene as a monomer, 3-(trimethoxysilyl)propyl acrylate (TMSPA) and azobisisobutyronitrile (AIBN) as an initiator and the reaction mixture is allowed to react. The reaction is carried out by agitating the reaction mixture in a cylindrical reactor.

Preparation Example 3. Preparation of Anisotropic Powder

The aqueous dispersion of the polystyrene-core shell (PC-CS) dispersion obtained as described above is mixed with styrene as a monomer, sodium 4-vinylbenzene sulfonate as a stabilizer and azobisisobutyronitrile (AIBN) as an initiator and the reaction mixture is heated to 75° C. to carry out reaction. The reaction is carried out by agitating the reaction mixture in a cylindrical reactor. In this manner, anisotropic powder having a symmetric shape is obtained.

Preparation Example 4. Hydrophilization

The aqueous dispersion of the anisotropic powder obtained as described above is mixed with N-[3-(trimethoxysilyl)propyl]ethylenediamine as a silane coupling agent and ammonium hydroxide as a reaction modifier and the reaction mixture is allowed to react to introduce a hydrophilic functional group. The reaction is carried out by agitating the reaction mixture in a cylindrical reactor.

Example 1

The amphiphilic anisotropic powder obtained from the above Preparation Example is used to obtain a macroemulsion composition having the composition as shown in the following Table 1. In a separate container, a nanoemulsion composition using a conventional surfactant is obtained according to the following Table 2. Then, the macroemulsion composition is mixed with the nanoemulsion composition at a weight ratio of 9:1 to obtain the composition of Example 1.

TABLE 1

| Ingredients | Amount (wt %) |
| --- | --- |
| Water | To 100 |
| Amphiphilic anisotropic powder | 2.5 |
| Preservative 1 (PhenoxyEthanol) | 0.3 |
| Preservative 2 (Ethylhexylglycerin) | 0.05 |
| Moisturizer (Butylene Glycerol) | 8 |
| Oil (Hydrogenated polydecane) | 10 |

TABLE 2

| Ingredients | Amount (wt %) |
| --- | --- |
| Surfactant (Hydrogenated lecithin) | 0.8 |
| Oil (Cetyl octanoate) | 10 |
| Oil (Squalane) | 10 |
| Skin conditioning agent (Cholesterol) | 0.8 |
| Skin conditioning agent (Hydroxypropyl bispalmitamide MEA) | 0.05 |
| Water | 65.85 |
| Moisturizer (Butylene glycol) | 8 |
| Moisturizer (glycerin) | 4 |
| Preservative (Phenoxyethanol) | 0.3 |
| Preservative (Ethylhexylglycerin) | 0.05 |
| Thickener (Xanthan gum) | 0.15 |

Test Example 1. Observation of Change in Emulsion Particles at High Temperature After sampling the composition of Example 1, the emulsion particles are observed with a microscope. Then, a change in particles is observed after storing the composition at a high temperature of 45° C. for 5 days.

After the observation, it is shown that a hybrid emulsion composition is obtained by forming larger emulsion particles (several tens of micrometers) and smaller emulsion particles (several nanometers) through the use of the amphiphilic anisotropic powder and conventional surfactant and simply mixing the particles physically. The hybrid emulsion composition may realize various feelings of use according to the mixing ratio of the emulsion compositions.

FIG. 1 shows microscopic images of the hybrid emulsion composition obtained by the individual emulsion mixing method according to an embodiment, wherein (a) shows a formulation obtained from emulsion particles using anisotropic powder (size: about several tens of micrometers) and nanoemulsion particles (size: about 200 nm) using a general surfactant, right after the preparation thereof, (b) and (c) show the emulsion particle sizes after storing the formulation for 2 weeks and 4 weeks, respectively, at a high temperature of 45° C., and (d) shows the result obtained by fluorescence imaging of the nanoemulsion in the sample. As can be seen from FIG. 1, the hybrid emulsion composition does not cause any change in particle size or coalescence of different particles even after storing it at a high temperature of 45° C. for 4 weeks. In addition, separation, precipitation and creaming are not observed and Ostwald ripening does not occur. The two different types of particles coexist stably and independently from each other.

Test Example 2. Observation of Particle Distribution of Emulsion Particles

The emulsion particle size of the hybrid emulsion composition according to Example 1 is determined by using Zetasizer Nano (Malvern) right after its preparation and after the lapse of 4 weeks at 45° C. The particle size distribution is shown in FIG. 2.

In FIG. 2, (a) shows that the particle size distribution right after the preparation is approximately 200 nm on average, (b) shows that the particle size distribution after the lapse of 4 weeks is approximately 190 nm on average. Thus, it can be seen that no significant difference in distribution is observed and the hybrid emulsion is maintained stably with time.

Test Example 3. Evaluation of Stability of Composition with Time

The hybrid emulsion composition according to Example 1 is determined for its stability while maintaining the composition at −15° C. to 60° C. for 18 weeks. The formulation is maintained stably without creaming or separation of oil at different temperatures, which suggests that the composition of Example 1 has high stability at different temperatures with the lapse of time.

FIG. 3 is a graph illustrating a change in viscosity of the hybrid emulsion composition according to Example 1 after maintaining it at 30° C. for 18 weeks. Measurement of viscosity is carried out by using Viscometer (LVDV-II+ PRO, BROOKFIELD, USA). It can be seen from the results of FIG. 3 that no significant change in viscosity is observed even at 30° C. for a long time, and thus the hybrid emulsion composition has high formulation stability.

As can be seen from the foregoing, the hybrid emulsion composition disclosed herein is maintained stably over a range of temperatures for a long time, while each of the macroemulsion particles and the nanoemulsion particles retain its particle size independently and is maintained stably. It is thought that this is because the emulsion using anisotropic powder and the conventional emulsion have a different emulsion system and cause little interaction at the interface between the two types of emulsion particles, and the emulsion particles of the emulsion using anisotropic powder maintain the emulsion interface firmly to prevent coalescence of particles.

While the exemplary embodiments have been shown and described, it will be understood by those skilled in the art that various changes in form and details may be made thereto without departing from the scope of this disclosure as defined by the appended claims. Therefore, it is intended that the scope of the present disclosure includes all embodiments falling within the spirit and scope of the appended claims.

The invention claimed is:

1. A hybrid emulsion composition having different emulsion particle sizes, the emulsion composition comprising macroemulsion particles having a size of 1 μm-100 μm and nanoemulsion particles having a size of 100 nm-900 nm,
   wherein the macroemulsion particles include amphiphilic anisotropic powder, wherein the macroemulsion is formed by being emulsified using the amphiphilic anisotropic powder;
   the amphiphilic anisotropic powder includes
       a first hydrophilic polymer spheroid and a second hydrophobic polymer spheroid;
       the first and second polymer spheroids are bound to each other with a structure in which one polymer spheroid at least partially infiltrates the other polymer spheroid; and
       the first polymer spheroid has a core-shell structure, and the shell has a siloxane,
       wherein the amphiphilic anisotropic powder does not include crosslinks, wherein the nanoemulsion particles include a surfactant comprising hydrogenated lecithin, wherein the macroemulsion particles and the nanoemulsion particles are present at a ratio of 5-9:5-1, and wherein the hybrid emulsion composition comprises the amphiphilic anisotropic powder in an amount of 0.1 to 15 wt % based on the total weight of the hybrid emulsion composition.

2. The hybrid emulsion composition according to claim 1, wherein the second polymer spheroid and the core of the first polymer spheroid comprise a vinyl polymer, and the shell of the first polymer spheroid comprises a copolymer of a vinyl monomer with a siloxane-containing compound.

3. The hybrid emulsion composition according to claim 2, wherein the vinyl polymer comprises polystyrene.

4. The hybrid emulsion composition according to claim 1, wherein the shell of the first polymer spheroid further include a hydrophilic functional group introduced thereto.

5. The hybrid emulsion composition according to claim 4, wherein the hydrophilic functional group is at least one selected from the group consisting of carboxylic acid group, sulfone group, phosphate group, amino group, alkoxy group, ester group, acetate group, polyethylene glycol group and hydroxyl group.

6. The hybrid emulsion composition according to claim 1, wherein the amphiphilic anisotropic powder has a symmetric shape or asymmetric snowman shape on the basis of the binding portion where the first polymer spheroid and the second polymer spheroid are bound to each other, wherein the asymmetric snowman shape comprises first polymer spheroid and the second polymer spheroid having difference in their size.

7. The hybrid emulsion composition according to claim 1, wherein the amphiphilic anisotropic powder has a particle size of 100-1500 nm.

8. A method for preparing the hybrid emulsion composition as defined in claim 1, comprising:

forming each of an emulsion composition containing an amphiphilic anisotropic powder for preparing macroemulsion particles having a size of 1 µm-100 µm and an emulsion composition containing a surfactant for preparing nanoemulsion particles having a size of 100 nm-900 nm, and mixing the emulsion compositions with each other.

* * * * *